United States Patent
Buehler

(10) Patent No.: US 6,709,635 B1
(45) Date of Patent: Mar. 23, 2004

(54) GAS SENSOR TEST CHIP

(75) Inventor: Martin Buehler, La Canada, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 09/496,127

(22) Filed: Feb. 1, 2000

Related U.S. Application Data

(60) Continuation of application No. 09/371,798, filed on Aug. 10, 1999, now Pat. No. 6,040,189, which is a division of application No. 08/820,877, filed on Mar. 21, 1997, now Pat. No. 5,945,069.
(60) Provisional application No. 60/013,826, filed on Mar. 21, 1996, and provisional application No. 60/014,772, filed on Mar. 22, 1996.

(51) Int. Cl.⁷ .............................................. G01N 27/00
(52) U.S. Cl. ........................ 422/98; 436/121; 205/787
(58) Field of Search ........................ 422/98; 436/121; 205/787

(56) References Cited

U.S. PATENT DOCUMENTS

| | | | | |
|---|---|---|---|---|
| 3,683,671 A | * | 8/1972 | Van Swaay ..................... 73/27 |
| 4,151,503 A | * | 4/1979 | Cermak et al. ............... 338/14 |
| 4,352,099 A | * | 9/1982 | Christen et al. ............. 340/633 |
| 4,516,071 A | * | 5/1985 | Buehler .................. 324/158 R |
| 4,571,292 A | * | 2/1986 | Liu et al. ..................... 204/412 |
| 4,654,624 A | * | 3/1987 | Hagan et al. ................. 338/25 |
| 4,938,928 A | * | 7/1990 | Koda et al. .................... 422/98 |
| 4,992,244 A | * | 2/1991 | Grate .......................... 422/98 |
| 5,034,192 A | * | 7/1991 | Wrighton et al. ........ 422/82.02 |
| 5,045,285 A | * | 9/1991 | Kolesar, Jr. ................. 204/400 |
| 5,071,770 A | * | 12/1991 | Kolesar, Jr. ................. 436/151 |
| 5,145,645 A | * | 9/1992 | Zakin et al. ................... 422/98 |
| 5,252,292 A | * | 10/1993 | Hirata et al. ................. 422/98 |
| 5,345,213 A | * | 9/1994 | Semancik et al. ............ 338/34 |
| 5,571,401 A | * | 11/1996 | Lewis et al. ................ 205/787 |
| 5,605,612 A | * | 2/1997 | Park et al. .................. 204/429 |
| 5,659,127 A | * | 8/1997 | Shie et al. ................. 73/31.05 |
| 5,698,089 A | * | 12/1997 | Lewis et al. ................ 205/787 |
| 5,756,879 A | * | 5/1998 | Yamagishi et al. ........ 73/28.01 |
| 5,759,493 A | * | 6/1998 | Raisanen ..................... 422/98 |
| 5,767,687 A | * | 6/1998 | Geist .......................... 324/663 |
| 5,779,980 A | * | 7/1998 | Hatfield ....................... 422/95 |
| 5,783,154 A | * | 7/1998 | Althainz et al. .............. 422/98 |
| 5,788,833 A | * | 8/1998 | Lewis et al. ................ 205/787 |
| 5,804,703 A | * | 9/1998 | Wind et al. ................ 73/25.01 |
| 5,830,412 A | * | 11/1998 | Kimura et al. ................ 422/90 |
| 5,891,398 A | * | 4/1999 | Lewis et al. ............. 422/82.02 |
| 5,911,872 A | * | 6/1999 | Lewis et al. ................ 205/787 |
| 5,945,069 A | * | 8/1999 | Buehler ....................... 338/34 |
| 5,951,846 A | * | 9/1999 | Lewis et al. ................ 205/787 |
| 5,959,191 A | * | 9/1999 | Lewis et al. ............... 73/31.05 |
| 6,010,616 A | * | 1/2000 | Lewis et al. ................ 205/787 |
| 6,013,229 A | * | 1/2000 | Lewis et al. ............. 422/82.02 |
| 6,017,440 A | * | 1/2000 | Lewis et al. ............. 205/777.5 |
| 6,040,189 A | * | 3/2000 | Buehler ....................... 436/151 |
| 6,046,054 A | * | 4/2000 | McGeehin et al. ......... 436/121 |
| 6,055,849 A | * | 5/2000 | Shiori et al. .................. 422/98 |
| 6,085,576 A | * | 7/2000 | Sunshine et al. .......... 73/29.01 |
| 6,093,308 A | * | 7/2000 | Lewis et al. ................ 205/787 |
| 6,128,945 A | * | 10/2000 | Shiori et al. ............... 73/31.06 |
| 6,234,006 B1 | * | 5/2001 | Sunshine et al. .......... 73/29.01 |
| 6,244,096 B1 | * | 6/2001 | Lewis et al. ................. 73/23.2 |

FOREIGN PATENT DOCUMENTS

WO     WO 98/36265     *   8/1998   ................. 21/35

* cited by examiner

*Primary Examiner*—Mark L. Bell
*Assistant Examiner*—Jennie Brown
(74) *Attorney, Agent, or Firm*—Fish & Richardson P.C.

(57) ABSTRACT

A polymeric gas sensor utilizes a variety of electrode geometries to generate varied responses to selective gases. The characteristic response to various gases of each electrode geometry permits the construction of a gas sensor having desirable and reproducible characteristic responses to specific gases. The gas sensor array of the invention produces characteristic responses from a plurality of sensors. These responses collectively produce a characteristic response pattern that can be used for the identification of specific gases with pattern recognition techniques.

10 Claims, 9 Drawing Sheets

GAS SENSOR TEST CHIP CHEMORESISTOR DIMENSIONS

COMB RESISTOR

| SENSOR | S0 | S1 | S2 | S3 |
|---|---|---|---|---|
| L(mil) | 20 | 5 | 20 | 5 |
| W(mil) | 20 | 20 | 5 | 5 |
| $N_S$ | 0.5 | 0.125 | 2 | 0.5 |

SERPENTINE RESISTOR

| SENSOR | S11 |
|---|---|
| L(mil) | 120 |
| W(mil) | 5 |
| $N_S$ | 24 |

U-BEND RESISTOR

| SENSOR | S4 | S5 | S6 | S7 |
|---|---|---|---|---|
| L(mil) | 10 | 5 | 10 | 5 |
| W(mil) | 10 | 10 | 20 | 5 |
| $N_S$ | 0.243 | 0.164 | 0.164 | 0.243 |

ISOLATION RESISTER

| SENSOR | S12 |
|---|---|
| L(mil) | 15 |
| W(mil) | 60 |
| $N_S$ | 0.25 |

CONTACT RESISTOR

| SENSOR | S8 | S9 | S10 |
|---|---|---|---|
| L(mil) | 5 | 20 | 45 |
| W(mil) | 30 | 30 | 30 |
| $N_S$ | 0.167 | 0.667 | 1.5 |

*FIG. 2*

GAS SENSOR TEST CHIP

This is a continuation of U.S. application Ser. No. 09/371,798, filed Aug. 10, 1999 (issued as U.S. Pat. No. 6,040,189), which is a divisional application of application Ser. No. 08/820,877, filed Mar. 21, 1997 (issued as U.S. Pat. No. 5,945,069), which claims the benefit of the U.S. Provisional Applications Serial No. 60/013,826 filed Mar. 21, 1996 and Ser. No. 60/014,772 filed Mar. 22, 1996, the entirety of which is incorporated by reference.

ORIGIN OF INVENTION

The invention described herein was made in the performance of work under a NASA contract, and is subject to the provisions of Public Law 95-517 (35 USC 202) in which the Contractor has elected to retain title.

1. Field of the Invention

The present invention describes a polymeric gas sensor. More specifically the present invention describes a polymeric gas sensor utilizing a variety of electrode geometries to generate varied responses to selected gases.

2. Background and Summary of the Invention

Atmospheric monitoring is increasingly required for industrial processes, environmental control, and health and safety reasons. Improved gas sensors have opened up new applications such as: control of air quality in places such as vehicle interiors, high traffic areas, coal mines and spacecraft; monitoring and control of industrial processes; ah early detection of fires; flue gas surveillance; breath analysis for diagnostic and therapeutic purposes; and control of combustion processes for both economic and environmental benefits.

Conventional techniques for gas sensing included the use of mass spectrometers, which are too large for many applications. Solid state gas sensors are increasingly used because they offer a number of advantages including small size and relatively low cost. Solid state gas sensors generally fall into three broad categories. Catalytic gas detectors burn flammable gases and detect the concentration of the flammable gas by the rise in temperature. Solid electrolyte sensors use ionic conduction to allow the generation of a concentration cell electro motive-force (EMF) between conducting species in solid and gas phases. Semiconducting oxide sensors employ the semiconducting properties of materials either in the form of high surface area, porous bodies, or in the form of thin, dense films. These include Silicon Carbide (SiC) and tin dioxide (SnO2) sensors.

Solid state gas sensors usually need to operate at relatively high temperatures. For example, most semiconducting oxide sensors operate at a few hundred degrees Celsius. High operating temperatures usually require high power consumption. This limits the usefulness of the sensor, particularly for battery powered applications. Thus it is an object of the present invention to provide a low power, compact, gas sensor array which operates at room temperature.

Polymer-based ("polymeric") gas sensors use a sensing material formed of thin films of conducting polymers. These sensors use organic polymers to detect gases via conductivity changes. Polymeric gas sensors (also referred to herein as "chemoresistors"), offer significant advantages. They operate at near room temperatures, and hence can be used for low power applications. Also, polymer-based sensors can be made to be very compact.

Polymeric gas sensors can be built into an array of sensors, where each sensor is designed to respond differently to different gases. For example, the gas sensitivity of each polymer in such an array is usually determined by the material's polymerization and dopant characteristics. Each element of the array measures a different property of the sensed sample. Each different gas sample presented to the sensor array hence produces unique patterns of collective sensor element responses. These patterns become "signatures" that are characteristic of a gas, or combination of gases. Sensor arrays may be combined with an automated data analysis system (such as a neural network) to identify specific vapors from the sensor output signatures. This kind of a gas sensor is often referred to as an "artificial nose." Because they are very sensitive in identifying different gases, artificial noses are opening up many new applications; these include monitoring food and beverage odors, automated flavor control, analyzing fuel mixtures, quantifying individual components of gas mixtures, etc.

It is important to perform real-time sensing and monitoring of hydrocarbon gases affecting the health of persons in isolated environments. For example, spacecraft often require sensing of hydrocarbon gases that are a byproduct of decomposition of hydrocarbon based chemicals. However, current low power sensors that detect hydrocarbons are not able to effectively distinguish among different hydrocarbon compounds. This suggests a need for low-power sensors that can effectively distinguish among different hydrocarbons.

The present inventors have recognized that polymer-based gas sensors have the potential to meet this need. However, the implementation of polymer-based gas sensor arrays is presently limited by a lack of reproducibility of their response to gases. The present inventors have recognized that the development of a practical, reproducible, polymer-based gas sensor array will require full characterization of the conductivity of the polymer films used in the array. This characterization will preferably include measurements of various aspects of the conduction mechanisms in the polymer film used in the sensors. These conduction parameters include sheet resistance, surface conduction, anisotropic conduction, film nonuniformity, and contact resistance. It is an object of the present invention to provide a technique for characterizing conduction parameters of polymer films used with polymeric gas sensor arrays and to determine the optiumum electrode geometry.

It is another object of the invention to use these fully characterized, reproducible polymer films to construct low power, hydrocarbon sensitive polymer-based gas sensor arrays.

SUMMARY OF THE INVENTION

The present inventors have discovered that the response of polymeric films to various gases depends on the shape of the sensor electrode in ways that enable reproducible characterization of the polymeric films. In particular, different geometric configurations of the electrodes in the polymeric films result in different characteristic responses to gases. These reproducible and distinctive responses facilitate the detection of gases because they produce unique and consistent patterns that are readily recognizable.

One aspect of the invention is a method of measuring responses of a gas sensor to predetermined gases. The method includes the steps of fabricating a gas sensor that has a plurality of resistor elements that share a common electrode. Each resistor element has a plurality of different electrode configurations. For example, in one embodiment these electrode configurations include: U-bend, comb and serpentine shapes. The resistor elements are then exposed to a predetermined known gases. Patterns of characteristic changes in the conductance of the resistor elements in response to exposure to the predetermined gases is then measured and stored.

Another aspect of the invention is a gas sensor fabricated on a substrate that includes a plurality of electrodes where each electrode has a plurality of shapes an dimensions. Polymer films are deposited over the electrodes. The polymer films have a conductivity that changes when the film is exposed to various gases as measured across the electrodes. A current measuring circuit is connected to the electrodes to measure these conductivity changes. An optimal geometric configuration for the electrode is selected based on prior tests of the film's response to various gases of interest. By having a electrode geometry as well as other factors that optimizes the polymer film's response to a particular gas, the gas sensor exhibits an improved ability to distinguish among different gases. The test sensor of the present invention permits the optimization of numerous other factors such as polymerization process by control of the polymerization heat using the heater elements, polymer film doping and other factors.

Another aspect of the present invention relates to the fabrication of gas sensors. Prior fabrication techniques utilizing gas polymer films. Previous gas sensors employed polymer films that needed to be patterned once applied. These included Bridge and Van Der Pauw resistor structures. The fabrication technique of the present invention does not require patterning after application of the polymer film. In this fabricating technique a plurality of electrodes having the desired geometric configurations are first deposited on the substrate. A polymer film is then deposited over the electrodes. A heater element may also be deposited prior to the polymer film to permit control of the polymerization process. The result is a simpler and less expensive fabrication process than those requiring patterning.

BRIEF DESCRIPTION OF THE DRAWING

These and other aspects of the invention will now be described in detail with reference to the accompanying drawings, wherein:

FIG. 2 shows chemoresistor dimensions used in the gas sensor chip in FIG. 1;

DESCRIPTION OF THE PREFERRED EMBODIMENTS

Presently preferred embodiments of the invention are set forth herein with reference to the accompanying drawings. The present invention includes: a test chip for characterizing gas sniffing polymer films; a polymer-based gas sensor with electrodes configured to optimize gas response patterns having improved reproducibility; and methods for producing the gas sensor and test chips. In each of these embodiments, gas is detected by gas-induced conductivity changes in polymers, such as polypyrroles.

Polypyrrole films containing different dopants and having different polymerization processes exhibit different conductivity changes in response to a given gas. The identity of the gas can be determined using pattern recognition techniques, such as neural networks, to recognize a unique signature pattern of responses of these films. Such a sensor can be built into a small, low powered, package that can monitor gas environment in remote places where gas is likely to pocket.

As discussed above, lack of reproducibility has limited the utilization of polymer-based gas sensors. The present invention addresses this issue by providing a device and method for characterizing the conductivity of polymer films used in gas sensors. Such characterization of reproducible parameters is needed so that a gas-induced pattern of changes in the conductivity of various chemoresistors can be used to recognize a gas based on the similarity of the observed pattern to previously observed patterns.

Gas Sensor Chip Layout

Figure 1:
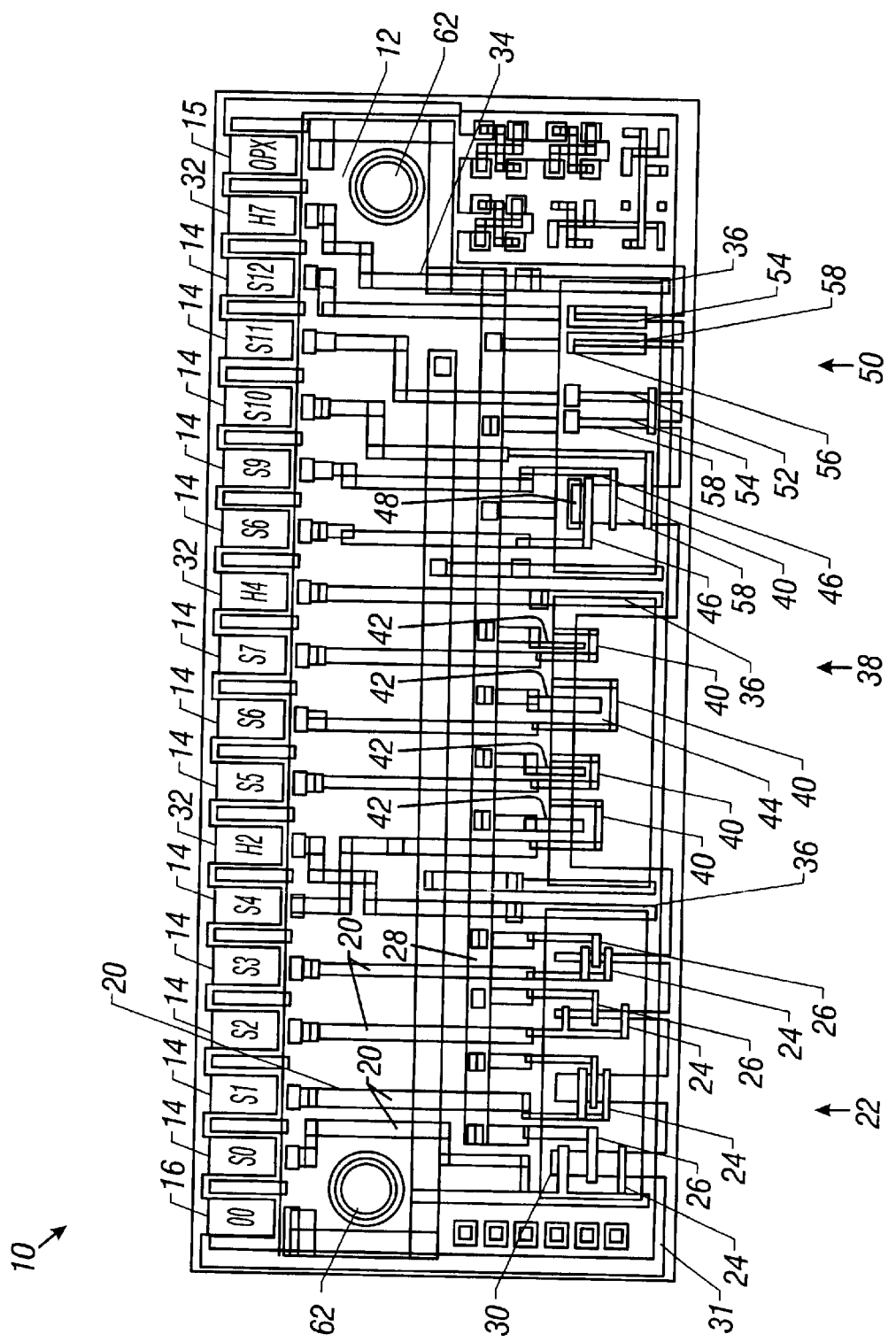
FIG. 1 shows a gas sensor chip layout of a polymeric gas sensor in accordance with the invention.

FIG. 1 shows a diagram of a gas sensor chip 10 in accordance with the invention. This sensor chip 10 is used to measure various aspects of the conduction mechanisms of polymer films. These parameters include sheet resistance, surface conduction, anisotropic conduction, film non-uniformity, and contact resistance. The repeatability of these parameters can be characterized as the film responds to various gases.

Repeatability is critical to accurate sensing. These sensors use pattern recognition techniques that are based on a comparison of new responses with previously measured signature responses of an array of polymer films in the presence of various gases. Variability in the film responses to a given gas exposure would result in response patterns that cannot be matched with expected patterns.

The sensor chip 10 comprises polymer films deposited in an array on the chip surface. Measurement circuitry, described below and shown in FIG. 3, sequentially places each polymer film element in the array, in the feedback loop of an operational amplifier configured as a current-to-voltage-converter. This circuit drives a constant current through each film individually and changes in conductivity are thereby detected.

Each polymer film element acts as a resistor in the circuit. A chemoresistor is a resistor that changes based on a chemical effect. Each chemoresistor has a different sensitivity to different gases. The specific response of each polymer to a gas is determined by various previously known factors such as polymerization process-and dopant characteristics. The response to a gas is also determined by the geometry of the chemoresistor electrodes, as demonstrated by using the techniques of the present invention.

In a preferred embodiment, the sensor chip 10 is fabricated using a two-conductor thick film technology. The conducting polymer film coats the region between a pair of gold electrodes. The use of gold electrodes essentially eliminates the electrode/polymer contact resistance which is found in other electrodes such as those that are aluminum-based. The fabrication technique of the invention is preferred to prior approaches such as Bridge and Van Der Pauw resistor structures. These kinds of resistors require the polymer film to be patterned using photolithographic techniques after they are applied. The present invention needs no patterning once the film is applied, greatly simplifying the fabrication process.

The chip uses various geometric formations of the chemoresistors for the purpose of characterizing and controlling the basic conduction mechanisms. For example, Comb and U-Bend Resistors are used for characterizing the basic conduction mechanisms. Also, the structure's geometry variations allow the separation of contact and sheet resistance. Since the films bridge between two electrodes contact resistance may exist where the electrode touches the film. A plot of the resistance versus distance between electrodes for various size electrodes can be used to extrapolate to zero distance; any resistance at that point equals the contact resistance.

The sensor chip 10 is formed on substrate 12 which is preferably a low temperature (800° C.) co-fired ceramic substrate fabricated using 125 μm line widths and spaces. The chips have seven screen printed layers. The chip includes thirteen contact pins 14 that allow access to thirteen different sensor electrode structures. Three contact pins 32 are for heaters used to control polymerization. Heaters also have utility in thermometry, electrical shielding and in describing absorbed gases. A seventeenth contact pin 16 is used for a ground. An eighteenth contact pin 18 is connected a common electrode in each chemoresistor through surface resistor 28. This contact pin 18 is used to place each chemoresistor, one at a time, in the feedback loop of an operational amplifier using multiplexing test circuitry, as described below. Each contact pin 14 is connected to a surface resistor 20 which in turn leads to an electrode in one chemoresistor.

The first four chemoresistors 22 have comb-shaped electrodes. Internal resistors 20 connect contact pins S0, S1, S2 and S3 to a first set 24 of Comb-shaped gold electrodes. These four chemoresistors are also identified herein by their corresponding contact pin number, S0, S1, S2 and S3, respectively. Each of the Comb electrodes 24 are disposed adjacent to a second gold electrode 26. The op amp contact pin 18 connects the gold electrode 26 through contact resistor 28. A polymer film 30 is applied as described below so that it contacts all of the Comb electrodes 24, 26, resulting in resistors 22. The Comb electrodes 22 are covered by an insulating glassy layer 31 except in the channel where the electrodes are exposed to the polymer film 30.

Heater contact pins 32 are connected via surface resistors 34 to one side of a set of heaters 36. The opposite side of each heater is connected to ground via surface contact 16. Each heater lies under a different polymer film to control temperature, and hence the polymerization process. Similarly, four U-Bend Resistors 38(also referred to as S4, S5, S6 and S7) include U-shaped gold electrodes 40 and 42. Each U-shaped gold electrode 40 is adjacent to a linear gold electrode 42 that is connected by an internal resistor 28 to the op amp contact pin 18. A single polymer film .44 is applied over all of the U-Bend electrodes 40 and 42 to form U-Bend Resistors 38.

Contact Resistors 49 (S8, S9 and S10) are arranged as shown, with gold electrodes 46 connected to a corresponding contact pin 14. Adjacent to the S8 electrode is another gold electrode 48 which is connected to the op amp contact pin 18. A Serpentine Resistor 50 includes gold contact 52 adjacent to contact 54, which is connected to the op amp contact pin 18.

An isolation Resistor 52 is connected to contact pin S12. This resistor 52 includes a gold contact 54 which is formed with the following geometric characteristics.

This gold contact 54 is adjacent to a similarly shaped gold contact 56 that is connected to the op amp contact pin 18. A single polymer film 58 is applied across the Contact 49, Serpentine 50 and Isolation 52 Resistors. Holes 60 and 62 are used to mount the chip on a spinner, as described below.

Common bussing is used to conserve pins. Electrode guarding is used to eliminate stray surface currents, and is accomplished by grounding all resistors except for the one under test. Kelvin voltage sensing avoids analog switch resistor voltage drops.

Each of the different types of chemoresistors (22, 44, 49, 50 and 52) have gas response characteristics that make it suitable for measuring particular conduction parameters. The various geometries are used to sort out the sheet and contact resistance. The Comb Resistors 22 are used to determine sheet and contact resistance. The U-Bend Resistors 38 are used to determine sheet resistance, and the Contact Resistor 49 is used to determine the sheet and contact resistance. The Serpentine Resistor 50 is used to determine the feasibility of that configuration for gas sensing.

The Isolation Resistor 52 is used to determine the degree of conductivity across the insulating glassy layer; that is, to determine how well the films are covering the insulator.

As shown in FIG. 1, different electrode configurations are employed to achieve a variety of geometries. For example, with the S0 Comb Resistor, conduction channels are relatively long and wide; in S1 they are short and wide; in S2 they are long and narrow; and in S3 they are short and narrow. Similar variations are also seen in the U-Bend and Contact Resistors. Many other variations may also be selected depending on the needs of the particular application.

FIG. 2 illustrates chemoresistor dimensions for all of the above-described chemoresistors. Each chemoresistor is identified by its associated contact pin number. The tables show the length and width of each chemoresistor as well as the number of squares (Ns), which is defined in detail below. The overall size of the gas sensor Chip 10 is 10 mm×24 mm.

Gas Sensor Chin Fabrication

Gas sensor chips 10 were prepared using films of polypyrrole (PPY) for the polymer films 30, 44 and 58. The PPY was prepared by dissolving $1.5 \times 10^{-3}$ moles pyrrole in 4 mL tetrahydrofuran (THF), $7.5 \times 10^{-4}$ moles phosphomolybdic acid in 4 mL THF, and mixing equal volumes of the two solutions. The polymer was applied using pipette deposition. Polymerization began immediately as evidenced by a color change. The polymer was allowed to form for about 15 minutes. A barrier tape was placed between the active electrodes and the connecting pins to prevent the solutions from wicking to the pins. The solution can be pipetted onto the test chip and spun using a conventional spinner for several seconds at 1500 rpm. Spinning is used to thin the deposited film. Alternatively, the film can be dipensed in a solvent which subsequently dissolves. The PPY was allowed to polymerize on the chip for a period of 30 minutes. During this time the resistance of each chemoresistor was monitored and found to be in the Mega-Ohm range.

The chips were then rinsed in methanol to remove unreacted pyrrole, excess THF, and excess acid, leaving an insoluble film of PPY. After removing non-conductive excess reactant and solvent, the resistance of the PPY films dropped by two orders of magnitude.

Gas Sensor Chip Test Circuitry

Figure 3:
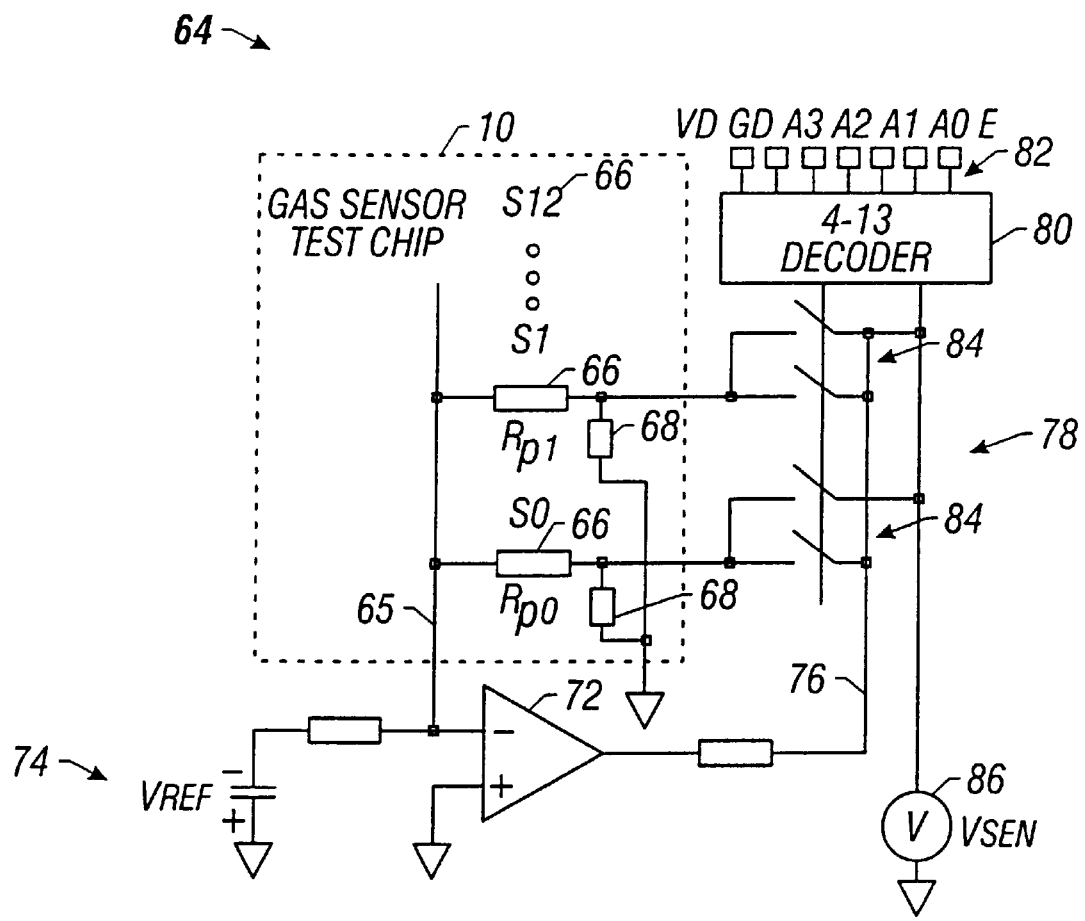
FIG. 3 shows a gas sensor test circuit of the present invention.

FIG. 3 shows a gas sensor chip 63 in accordance with the invention, connected to associated test circuitry. A test circuit 64 sequentially places each chemoresistor in the feedback loop of an operational amplifier. Each chemoresistor 66 is connected to a peripheral resistor 68 leading to ground.

A test chip op amp contact pin 65 is connected to one input of an amplifier 72. A voltage source ($V_{ref}$) 74 is also connected to this op amp input. The other op amp input is connected to ground. The op amp output 76 is connected sequentially to a single contact pin associated with the desired chemoresistor 66. This is done by use of a multiplexer 78, which includes a decoder 80. Multiplexer inputs 82 on the decoder 80 allow the desired chemoresistor 66 to be selected. A series of switches 84 are selectively opened and closed under control of the decoder 80. When the correct switch 84 is activated it will connect the desired chemoresistor 66 to the operational amplifier circuit based on the state of input pins 82.

The operational amplifier 72 is a current-to-voltage converter; a constant current ($V_{ref}$) is driven through each selected chemoresistor 66. The voltage resulting from the current in the selected chemoresistor 66 is then measured, stored, and/or displayed using voltage sensor 86. Test circuit 64 allows parts per million (PPM) changes in conductivity to be detected.

Test Results

Figure 4:
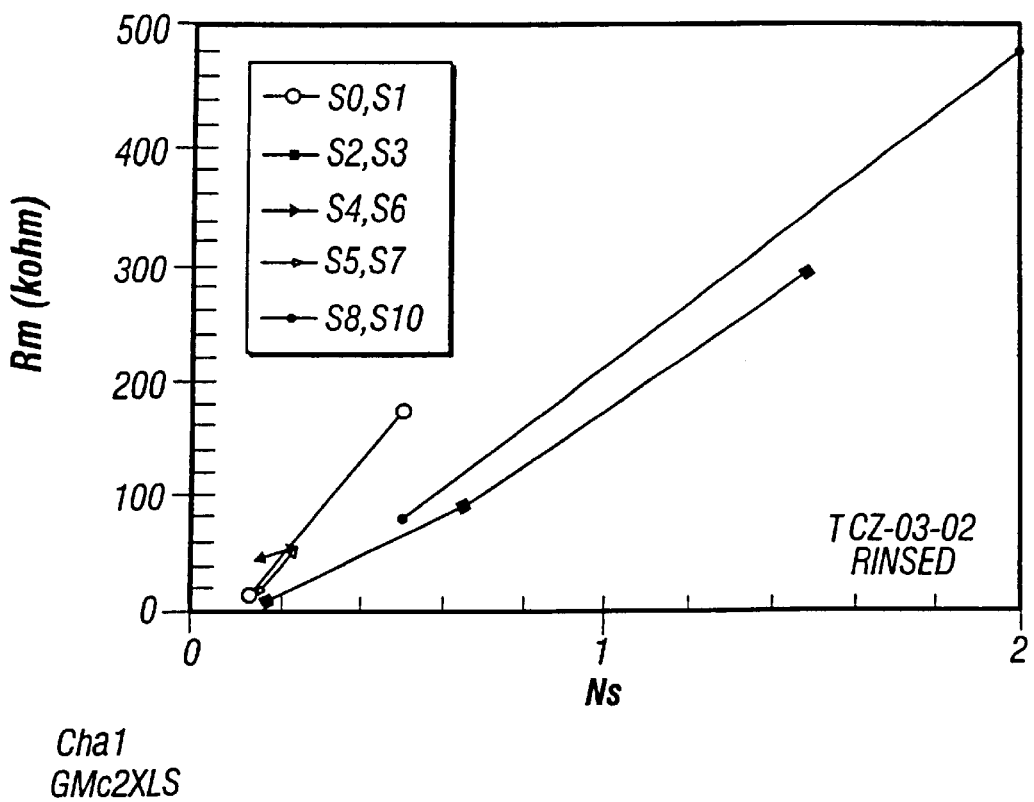
FIG. 4 shows resistance values for the chemoresistors in the chip in FIG. 1.

FIG. 4 shows measured resistor values from eleven chemoresistors on one example of a gas sensor chip constructed in accordance with the invention. The graph illustrates the variation in measured resistance (Rm) as a function of the number of squares Ns. The resistors have a linear current-voltage characteristic. The resistance is given by R=RsNs where Rs is the sheet resistance. For Comb Resistors 22, $$Ns=L/2W,$$

where L is the channel length and W is the channel width. For U-Bend Resistors 38, $$Ns=1/(2.111+2W/L).$$

This equation can be derived from the U-Bend resistor shown in FIG. 47 of the following article: P. M. Hill, "Resistance Calculations for Thin Film Patterns," *Thin Solid Films*, Vol. 1, 277–295 (1976/68), which is herein incorporated by reference. For the Contact Resistor test structure:

$$R=\rho c/W+RsNs$$

where $\rho c$ is the contact resistance and Ns=L/W.

Sheet resistance is about 50 K ohms per square when calculated using the slope of the curves in FIG. 4. Since the curves intercept close to the origin, the contact resistance is small. Detailed evaluation of the results is limited because the film appears to vary in thickness. This is evident in the nonlinear behavior of contact resistor (S8 to S10), as represented by triangles in FIG. 4. FIG. 4 also shows that the sheet resistance is higher between S8 and S9 than between S8 and S10. This can be explained by a thicker, hence more conducting, film near the edge of the chip.

The percent resistance change of chemoresistors to methanol (MeOH), ethanol (EtOH), 2-propanol (PrOH), and water (HOH) is shown in FIGS. 5 to 9, where the initial resistance is given in units of KΩ. During tests, the sensor was exposed to a saturated atmosphere of each compound. The sensor was exposed to air between these exposures.

Figure 5:
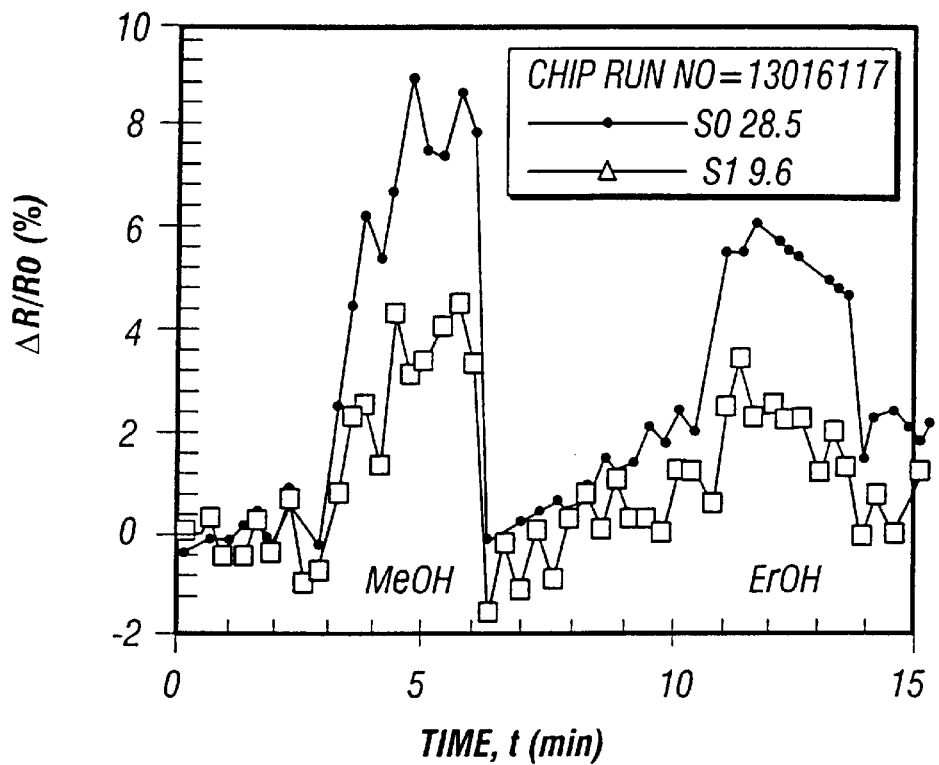
FIG. 5 shows the Comb Resistor response to methanol and alcohol for a first gas sensor chip of one embodiment of the invention.
Figure 6:
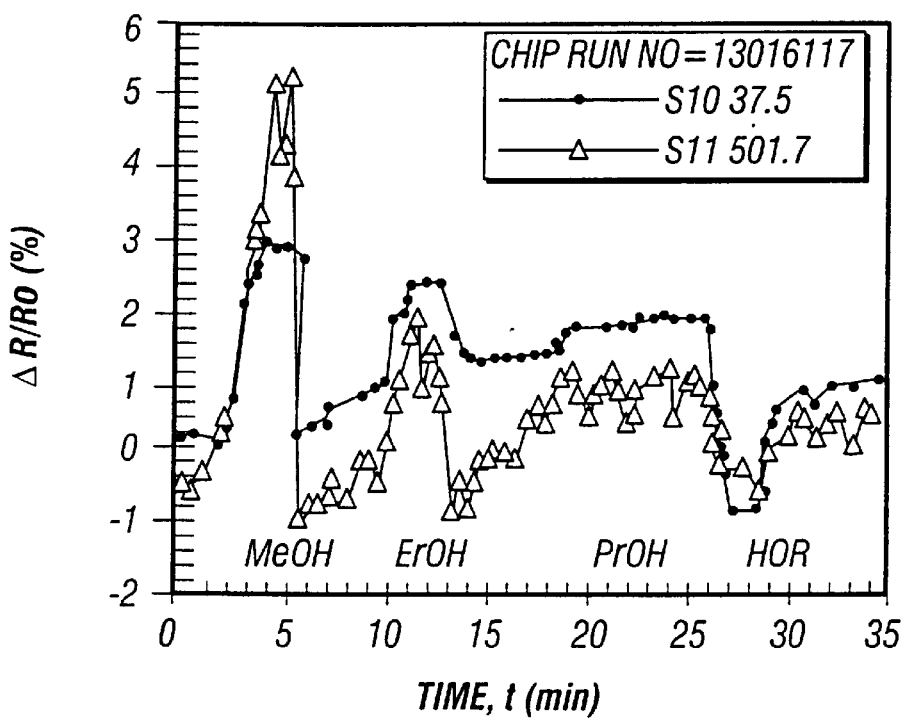
FIG. 6 shows Contact and Serpentine Resistor response to various gases for a first gas sensor chip of one embodiment of the invention.

The gas response for a first sample test chip built in accordance with the invention is shown in FIGS. 5 and 6. In FIG. 5; the response for sensors S0 and S1 indicates that the resistance changed by nearly 10 percent. MeOH has the greatest effect. The response to EtOH shows a characteristic declining resistance during exposure. This behavior was observed in other chips as explained below.

The responses shown in FIG. 6 represents a sequential exposure to four vapors for sensors S10 and S11. The alcohol response is always positive; whereas, the water response is negative. The S11 response has a low noise behavior when compared to the response of sensor S10. This low noise behavior is essential to PPM gas detection where PPM resistance changes are expected. Hence, based on these results, the present invention reveals that, in general, resistors using the geometry of the Serpentine Resistor will be preferred to that of the Contact Resister when PPM resistance changes need to be measured. This is but one of many ways in which the present invention enables the selection of the optimized electrode configuration to improve a gas sensor's ability to discriminate particular gases and combinations of gases.

Figure 7:
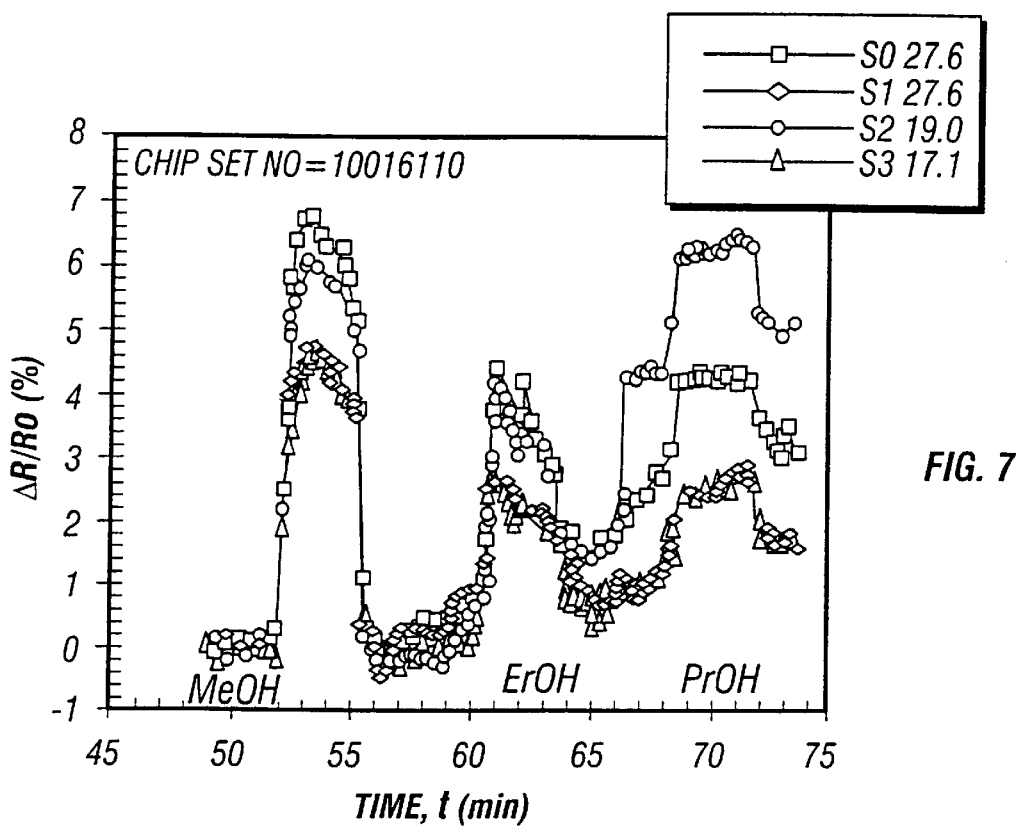
FIG. 7 shows a Comb Resistor response to various gases of a second gas sensor chip of the invention.
Figure 8:
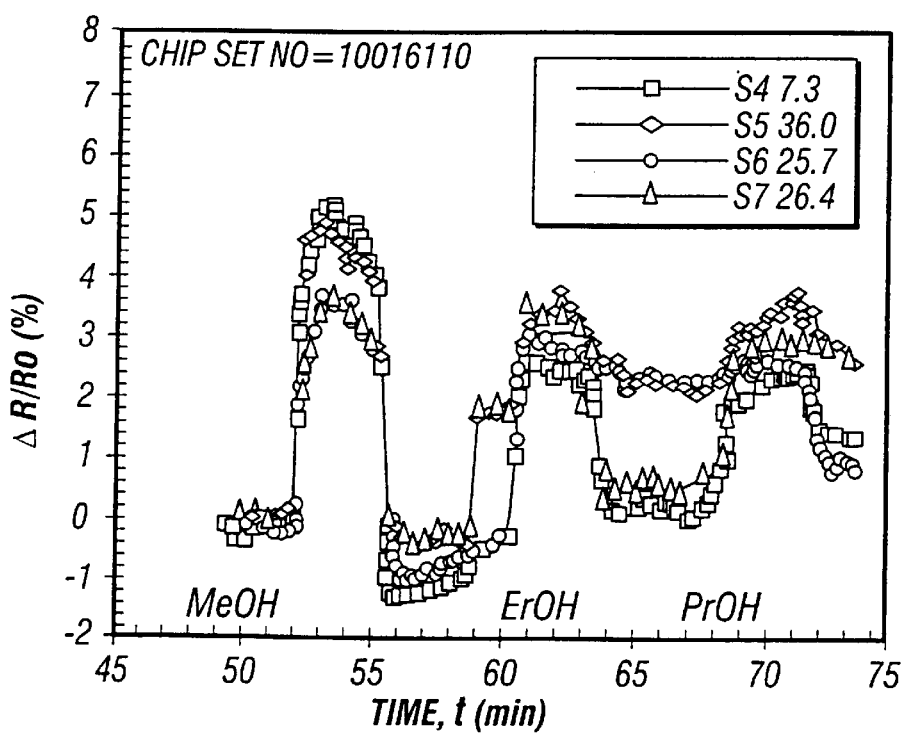
FIG. 8 shows a U-Bend Resistor response to various gases for a second gas sensor chip of the invention.
Figure 9:
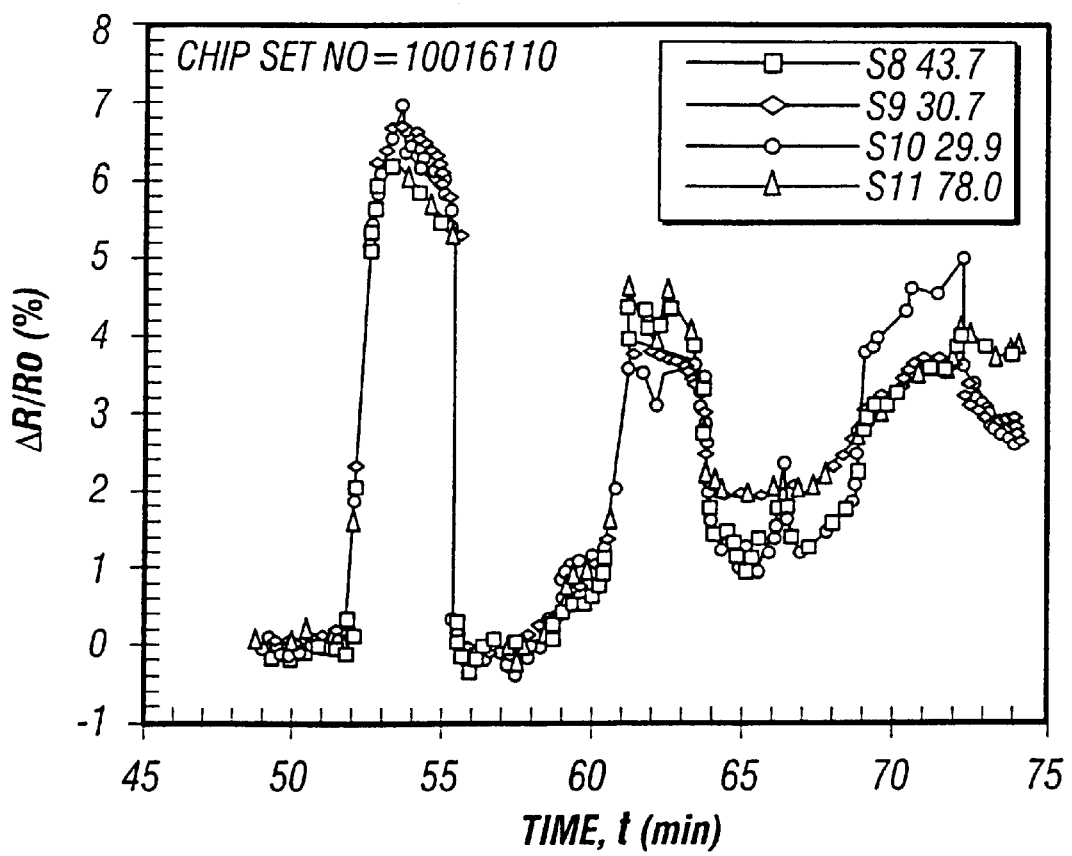
FIG. 9 shows Contact Resistor and Serpentine Resistor response to various gases for a second gas sensor chip of the invention.

In FIGS. 7–9, the gas response of a second test chip is shown for all resistors when exposed to MeOH, EtOH, and PrOH. Note that the magnitude of the resistance change is inversely proportional to the molecular weight of the vapor. The sensors have a time response that is less than the 15 second sampling period. The curves also have a characteristic shape that depends on the vapor identity. That is, the MeOH response has a relatively slow rise and fall over the period of exposure. The EtOH response has a declining behavior during exposure and exhibits a unique dip. This dip might be due to film swelling. The PrOH response shows a flat top behavior. Knowledge of these characteristic slopes will greatly facilitate the identification of gases using pattern recognition techniques.

The sensors in all of the above examples exhibit a characteristic response that clearly depends on electrode geometry. For instance, the Comb Resistor response appears to always be greatest for sensor S0 and least for sensor S2. The sensor S2 has a narrow conduction channel; whereas S0 has a wider conduction channel. That is, 2W/L is 0.5 for S2; for S0 it is 2. It is possible that response is affected by the width of the conducting channel, which determines the proximity of the conducting channel to the insulating walls. Also, the wider channel may have greater film thickness. The U-Bend Resistors, however, seem to exhibit a more uniform behavior between themselves. This may be due to the lack of insulating walls in the vicinity of these structures. A top layer of dielectric, the insulating glassy layer, used to hide the electrodes, except where they are to be exposed. The edges of these layers are the insulating walls.

These results illustrate the inventor's discovery and use of the influence of resistor geometry on sensor response. With this understanding, sensor parameters such as noise levels and sensitivity to particular gases can be optimized by the techniques of the present invention. In particular, this optimization is done by analyzing a film's response to the particular gas, and by choosing the appropriate resistor geometry, and other parameters based on the results. Electrode geometries that produce clear and distinctive response patterns can be selected for applications involving difficult to discriminate gases and combinations of gases. That is, the larger and more distinctive a response is (e.g. a notch, falling resistance, etc.) for a given gas, the easier it will be for a pattern recognition system to distinguish and identify a particular gas.

Gas Sensor System

Figure 10:
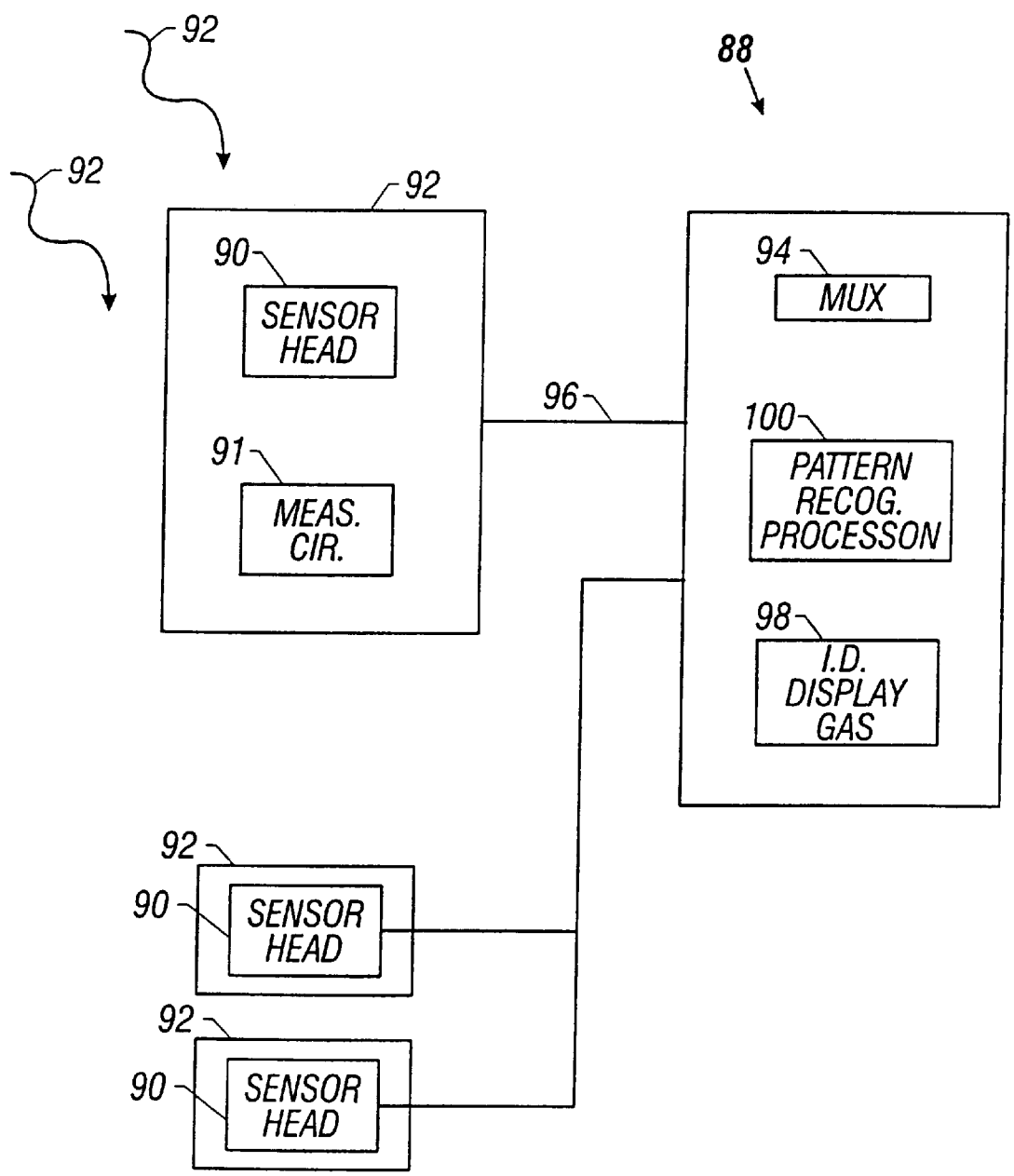
FIG. 10 shows a gas sensor system in accordance with one embodiment of the invention.

Using the present invention, substantially reproducible and well characterized polymer film gas sensors can be achieved. These sensors can be used in an "electronic nose" to detect various gases. FIG. 10 shows one such example. This gas sensor system 88 exploits the above-discussed characteristic responses that depend, in part, on resistor geometry. In particular, a polymer film gas sensor head 90 is constructed using the techniques described above for generating the gas sensor chip 10. Also packaged within sensor head package 92 will be a measurement circuit 91 such as the measurement circuit 64 shown in FIG. 3.

Resistor geometries are selected so as to optimize the desired response to the particular gases being sensed. Other factors that alter the sensor response to different gases 92 can also be manipulated to optimize the detect ability of various gases under consideration. Besides resistor geometry, these factors include film material, polymerization process, which can be selectively controlled by the use of heaters 36, the dopant and doping level in the polymer film. For example, carbon is one dopant that can be added to the films.

The responses of gas sensor head 90 to specific gases can be fully characterized using a combination of conventional gas sensor characterization techniques and the techniques of the present invention. The sensor head 90 is contained in a conventional sensor head package 92 which may be attached to a computer 94. Computer 94 serves as power source, data acquisition controller, data analyzer, and data IO.

A single computer 94 may be connected to a plurality of sensor heads 92. For example, in a space station application numerous sensor heads 92 may be placed in many locations throughout the space station to sniff the local gas environment. Gas analysis results can be displayed on the computer screen 98. Data can be downlinked to the ground by numerous methods including astronaut verbal readout, video readout, serial IO (RS-242) link to the station's data system, and floppy disk.

Data analyzer 100 will compare a pattern of response of the individual chemoresistors in the gas sensor head 90 to previously measured and characterized responses for known gases. The matching of these patterns can be performed using a number of techniques, including neural networks. See J. W. Gardner and P. N. Bartlett, "Performance Definition and Standardization of Electronic Noses," *The 8th International Conference on Solid-State Sensors and Actuators and Eurosensors IX*, Stockholm, Sweden, 671–674 (June 1995), which is herein incorporated by reference. See also P. Keller.et al. "Neural Network Based Sensor Systems for Manufacturing Applications," *Advance Information Systems and Technology Conference*, Doc. No. PNL-Essay-23252, Williamsburg, Va. (March 1994), which is incorporated by reference. Further details of conventional techniques for characterizing gas sensors are well known.

Figure 11:
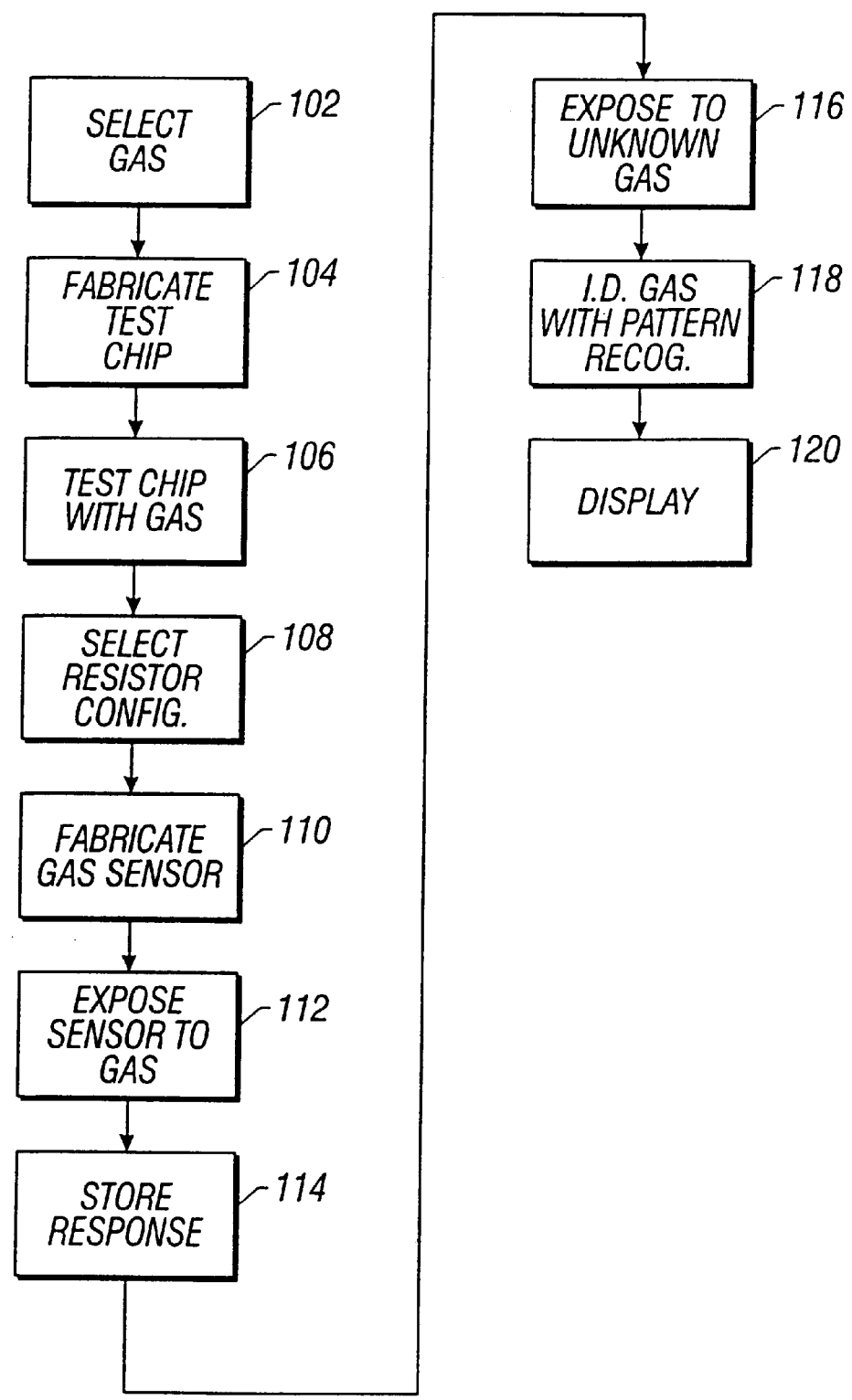
FIG. 11 shows a flow chart of the method of identifying gases in accordance with the invention.

FIG. 11 shows a flowchart of a method of identifying gases in accordance with the preferred embodiment of the invention. First the gases to be detected are selected, as shown in block 102. Next a test chip is fabricated incorporating a variety of electrode geometries, as shown in block 104. Next a series of tests are performed measuring the response of each electrode to various gases, as shown in block 106. These test results are then analyzed to select the optimum electrode configurations for maximizing detectability and reproducibility, as shown in block 108.

A gas sensor incorporating the selected resistor configurations is then fabricated, as shown in block 110. The gas sensor is then exposed to selected ones of the gases to be detected in block 112. The characteristic responses to each known gas are then stored, as shown in block 114. In block 118 the sensor is then exposed to an unknown gas in block 116, and pattern recognition techniques are employed to compare the response of the unknown gas to the stored characteristic responses for predetermined gases. Finally, the pattern recognition system displays an identification of the unknown gas in block 120.

Gas sensor chip 10 in the preferred embodiment is useful as a test chip to identify polymer films with repeatable and desirable gas sensing characteristics. The same chip may be used as a gas sensor employing preselected parameters, including electrode geometry, that are derived using the techniques of the invention. The invention will find maximum utility with applications using conducting films that don't have to be patterned subsequent to their deposition.

Although only a few embodiments have been described in detail above, those having ordinary skill in the art will certainly understand that many modifications are possible in the preferred embodiment without departing from the teachings thereof.

All such modifications are intended to be encompassed within the following claims.

What is claimed is:

1. A gas sensor test chip, comprising:
a single substrate having a plurality of gas sensor resistor elements thereon, each said gas sensor resistor elements having a first gas sensor electrode having a different geometric configuration from one or more other first gas sensor electrodes in the test chip.

2. The gas sensor test chip of claim 1, wherein each gas sensor resistor element has a different reaction to each of a number of different gases.

3. The gas sensor test chip of claim 1, wherein each gas resistor element includes a second gas sensor electrode separated from the first gas sensor electrode by a polymer film.

4. The gas sensor test chip of claim 3, wherein said polymer film comprises a polypyrrole film.

5. The gas sensor test chip of claim 3, wherein said polymer film comprises a polymer sensor layer covering the first gas sensor electrodes in a plurality of said gas sensor resistor elements.

6. The gas sensor test chip of claim 1, wherein each of said first gas sensor electrodes is connected to a different one of a plurality of contact pins.

7. The gas sensor test chip of claim 1, wherein each of said second gas sensor electrodes is connected to a common contact pin.

8. The gas sensor test chip of claim 7, wherein said common contact pin is connected to an operation amplifier including test circuitry.

9. The gas sensor test chip of claim 1, wherein at least one of said first gas sensor electrodes has a U-shaped geometric configuration.

10. The gas sensor test chip of claim 1, wherein at least one of said first gas sensor electrodes has a comb-shaped geometric configuration.

* * * * *